United States Patent
Dietz et al.

(10) Patent No.: US 7,259,845 B2
(45) Date of Patent: Aug. 21, 2007

(54) DISPOSABLE OPTICAL CUVETTE CARTRIDGE WITH LOW FLUORESCENCE MATERIAL

(75) Inventors: Louis J. Dietz, Mountain View, CA (US); Christopher E. Todd, San Jose, CA (US)

(73) Assignee: PPD Biomarker Discovery Sciences LLC, Wilmington, NC (US)

( * ) Notice: Subject to any disclaimer, the term of this patent is extended or adjusted under 35 U.S.C. 154(b) by 0 days.

(21) Appl. No.: 11/185,430

(22) Filed: Jul. 19, 2005

(65) Prior Publication Data

US 2006/0119844 A1    Jun. 8, 2006

Related U.S. Application Data

(63) Continuation of application No. 10/421,638, filed on Apr. 22, 2003, now Pat. No. 6,937,330, which is a continuation-in-part of application No. 09/552,872, filed on Apr. 20, 2000, now Pat. No. 6,552,784.

(60) Provisional application No. 60/130,876, filed on Apr. 23, 1999, provisional application No. 60/130,918, filed on Apr. 23, 1999, provisional application No. 60/130,875, filed on Apr. 23, 1999.

(51) Int. Cl.
*G01N 1/10* (2006.01)

(52) U.S. Cl. ....................... 356/246

(58) Field of Classification Search ............ None
See application file for complete search history.

(56) References Cited

U.S. PATENT DOCUMENTS

| | | | |
|---|---|---|---|
| 3,552,865 A | 1/1971 | Leung et al. | |
| 3,690,836 A | 9/1972 | Buissier et al. | |
| 3,997,298 A | 12/1976 | McLafferty et al. | |
| 3,999,047 A | 12/1976 | Green | |
| 4,405,235 A | 9/1983 | Rossiter | |
| 4,426,451 A | 1/1984 | Columbus | |
| 4,643,570 A | 2/1987 | Maechler et al. | |
| 4,752,888 A | 6/1988 | Yoshihara | |
| 4,761,381 A | 8/1988 | Blatt et al. | |
| 4,786,813 A | 11/1988 | Svanberg et al. | |
| 4,844,617 A | 7/1989 | Kelderman et al. | |

(Continued)

FOREIGN PATENT DOCUMENTS

DE    19829094    1/2000

(Continued)

OTHER PUBLICATIONS

Gygi et al. (1999) Nat. Biotech. 17:994-999.
do Lago et al. (1995) Anal. Chim. Acta, 310: 281-288.
Windig et al. (1996) Anal. Chem., 68: 3602-3606.
Chace (2001) Chem. Rev. 101:445-477.
Breen, et al. (2000) Electrophoresis 21:2243-2251.
Koradi et al. (1998) J. Mag. Res. 135:288-297.

(Continued)

*Primary Examiner*—Michael P. Stafira
(74) *Attorney, Agent, or Firm*—Sheridan Ross P.C.

(57) ABSTRACT

A disposable cuvette cartridge for optical measurements is formed from three flexible thin layers. The middle layer is an adhesive sheet with cut out regions, typically between 30 and 50, serving as optical chambers bounded by the two outer layers. Inlet and vent holes in one of the outer sheets provide access to the optical chambers. At least one of the outer sheets is made of a material having low fluorescence, such as a cyclo-olefin copolymer. With its low background fluorescence, the cuvette cartridge is useful for high-throughput fluorescence measurements of biological samples.

9 Claims, 4 Drawing Sheets

U.S. PATENT DOCUMENTS

| | | | |
|---|---|---|---|
| 4,849,330 A * | 7/1989 | Humphries et al. | ...... 205/777.5 |
| 4,963,498 A | 10/1990 | Hillman et al. | |
| 5,072,382 A | 12/1991 | Kamentsky | |
| 5,091,652 A | 2/1992 | Mathies et al. | |
| 5,119,315 A | 6/1992 | Kemp et al. | |
| 5,127,730 A | 7/1992 | Brelje et al. | |
| 5,192,980 A | 3/1993 | Dixon et al. | |
| 5,239,178 A | 8/1993 | Derndinger et al. | |
| 5,274,240 A | 12/1993 | Mathies et al. | |
| 5,304,810 A | 4/1994 | Amos | |
| 5,377,003 A | 12/1994 | Lewis et al. | |
| 5,412,208 A | 5/1995 | Covey et al. | |
| 5,430,542 A | 7/1995 | Shepard | |
| 5,446,532 A | 8/1995 | Yamazaki | |
| 5,453,505 A | 9/1995 | Lee et al. | |
| 5,456,252 A | 10/1995 | Vari et al. | |
| D366,938 S | 2/1996 | Shartle et al. | |
| 5,492,833 A | 2/1996 | Rodriguez et al. | |
| 5,523,573 A | 6/1996 | Hanninen et al. | |
| 5,532,873 A | 7/1996 | Dixon | |
| 5,547,849 A | 8/1996 | Baer et al. | |
| 5,556,764 A | 9/1996 | Sizto et al. | |
| 5,578,832 A | 11/1996 | Trulson et al. | |
| 5,585,246 A | 12/1996 | Dubrow et al. | |
| 5,592,402 A | 1/1997 | Beebe et al. | |
| 5,627,041 A | 5/1997 | Shartle | |
| D382,648 S | 8/1997 | Shartle et al. | |
| 5,658,735 A | 8/1997 | Lee | |
| D383,852 S | 9/1997 | Shartle et al. | |
| 5,672,869 A | 9/1997 | Windig et al. | |
| 5,682,038 A | 10/1997 | Hoffman | |
| 5,687,964 A | 11/1997 | Stephan et al. | |
| 5,689,110 A | 11/1997 | Dietz et al. | |
| 5,692,220 A | 11/1997 | Diamond et al. | |
| 5,710,713 A | 1/1998 | Wright et al. | |
| D391,373 S | 2/1998 | Shartle | |
| 5,713,364 A | 2/1998 | Debaryshe et al. | |
| 5,726,751 A | 3/1998 | Altendorf et al. | |
| 5,734,058 A | 3/1998 | Lee | |
| 5,736,410 A | 4/1998 | Zarling et al. | |
| 5,739,000 A | 4/1998 | Bierre et al. | |
| 5,741,411 A | 4/1998 | Yeung et al. | |
| D395,708 S | 6/1998 | Shartle | |
| 5,795,729 A | 8/1998 | Lee | |
| 5,814,820 A | 9/1998 | Dong et al. | |
| 5,832,826 A | 11/1998 | Mack et al. | |
| 5,867,610 A | 2/1999 | Lee et al. | |
| 5,871,946 A | 2/1999 | Lucas et al. | |
| 5,885,841 A | 3/1999 | Higgs, Jr. et al. | |
| 5,910,287 A | 6/1999 | Cassin et al. | |
| 5,912,134 A | 6/1999 | Shartle | |
| 5,932,428 A | 8/1999 | Dubrow et al. | |
| 5,962,238 A | 10/1999 | Sizto et al. | |
| 5,981,180 A | 11/1999 | Chandler et al. | |
| 5,995,989 A | 11/1999 | Gedcke et al. | |
| 6,002,986 A | 12/1999 | Mito | |
| 6,008,490 A | 12/1999 | Kato | |
| 6,008,896 A | 12/1999 | Sabsabi et al. | |
| 6,017,693 A | 1/2000 | Yates | |
| 6,059,724 A | 5/2000 | Campbell | |
| 6,063,338 A | 5/2000 | Pham et al. | |
| 6,066,216 A | 5/2000 | Ruppel, Jr. | |
| 6,072,624 A | 6/2000 | Dixon et al. | |
| 6,091,492 A | 7/2000 | Strickland et al. | |
| 6,093,573 A | 7/2000 | Beamer et al. | |
| 6,103,479 A * | 8/2000 | Taylor | ......... 435/7.2 |
| 6,104,945 A | 8/2000 | Modell et al. | |
| 6,112,161 A | 8/2000 | Dryden et al. | |
| 6,133,046 A | 10/2000 | Clerc | |
| 6,134,002 A | 10/2000 | Stimson et al. | |
| 6,138,117 A | 10/2000 | Bayardo | |
| 6,147,344 A | 11/2000 | Annis et al. | |
| 6,165,541 A * | 12/2000 | Merchant et al. | .......... 427/2.11 |
| 6,200,532 B1 | 3/2001 | Wu et al. | |
| 6,207,955 B1 | 3/2001 | Wells et al. | |
| 6,215,892 B1 | 4/2001 | Douglass et al. | |
| 6,229,603 B1 | 5/2001 | Coassin et al. | |
| 6,229,635 B1 | 5/2001 | Wulf | |
| 6,232,114 B1 | 5/2001 | Coassin et al. | |
| 6,236,945 B1 | 5/2001 | Simpson et al. | |
| 6,253,162 B1 | 6/2001 | Jarman et al. | |
| 6,278,794 B1 | 8/2001 | Parekh et al. | |
| 6,334,099 B1 | 12/2001 | Grace et al. | |
| 6,376,843 B1 | 4/2002 | Palo | |
| 6,377,842 B1 | 4/2002 | Pogue et al. | |
| 6,388,788 B1 | 5/2002 | Harris et al. | |
| 6,391,649 B1 | 5/2002 | Chait et al. | |
| 6,400,487 B1 | 6/2002 | Harris et al. | |
| 6,421,612 B1 | 7/2002 | Agrafiotis et al. | |
| 6,449,584 B1 | 9/2002 | Bertrand et al. | |
| 6,514,767 B1 | 2/2003 | Natan | |
| 6,526,299 B2 | 2/2003 | Pickard | |
| 6,552,784 B1 | 4/2003 | Dietz et al. | |
| 6,590,204 B2 | 7/2003 | Baranov | |
| 6,603,537 B1 | 8/2003 | Dietz et al. | |
| 6,620,591 B1 | 9/2003 | Dunlay et al. | |
| 6,625,546 B2 | 9/2003 | Sepetov et al. | |
| 6,642,059 B2 | 11/2003 | Chait et al. | |
| 6,646,271 B2 | 11/2003 | Yokokawa et al. | |
| 6,687,395 B1 | 2/2004 | Dietz et al. | |
| 6,753,966 B2 | 6/2004 | Von Rosenberg | |
| 6,787,761 B2 | 9/2004 | Hastings | |
| 6,800,860 B2 | 10/2004 | Dietz et al. | |
| 6,835,927 B2 | 12/2004 | Becker et al. | |
| 6,846,638 B2 * | 1/2005 | Shipwash | .................. 435/7.1 |
| 6,858,435 B2 | 2/2005 | Chervet et al. | |
| 6,873,915 B2 | 3/2005 | Hastings | |
| 6,937,330 B2 | 8/2005 | Dietz et al. | |
| 6,950,185 B1 | 9/2005 | Da Silva et al. | |
| 6,962,818 B2 | 11/2005 | Schneider et al. | |
| 6,979,830 B2 | 12/2005 | Dietz et al. | |
| 2001/0019829 A1 | 9/2001 | Nelson et al. | |
| 2001/0055812 A1 * | 12/2001 | Mian et al. | ................... 436/45 |
| 2002/0049152 A1 | 4/2002 | Nock et al. | |
| 2002/0053545 A1 | 5/2002 | Greef | |
| 2002/0095419 A1 | 7/2002 | Parce | |
| 2002/0102610 A1 | 8/2002 | Townsend et al. | |
| 2002/0123055 A1 | 9/2002 | Estell et al. | |
| 2002/0141051 A1 | 10/2002 | Vogt et al. | |
| 2003/0087322 A9 | 5/2003 | Aebersold et al. | |
| 2004/0257576 A1 | 12/2004 | Kirsch et al. | |
| 2006/0000984 A1 | 1/2006 | Wolleschensky et al. | |

FOREIGN PATENT DOCUMENTS

| | | |
|---|---|---|
| EP | 0296136 | 12/1988 |
| EP | 0421736 | 4/1991 |
| EP | 0681177 | 11/1995 |
| EP | 0969283 A1 | 1/2000 |
| GB | 1 407 247 | 9/1975 |
| WO | WO-97 43732 | 11/1997 |
| WO | WO-98/16661 | 4/1998 |
| WO | WO-00/67017 | 11/2000 |
| WO | WO-00 70340 | 11/2000 |
| WO | WO-01/35266 | 5/2001 |
| WO | WO-01 44269 | 6/2001 |
| WO | WO-2088819 | 11/2002 |

OTHER PUBLICATIONS

Stein (1999) J. Am. Soc. Mass Spectrom. 10:770-81.
Schoonjans et al. (2000) J. Pharm. & Biomed. Analysis 21:1197-1214.
Fiehn et al. (2000) Nat. Biotech. 18:1157-1161.
Chelius et al. (2002) J. Proteome Res. 1:317-323.

Bryant et al. (2001) Rapid Commun. Mass Spectrom. 15:418-427.
Wang et al. (1987) Analytical Chemistry 59:649-654.
Aach & Church (2001) Bioinformatics 17:495-508.
Nielsen et al. (1998) J. of Chromatography A. 805:17-35.
Bylund et al. (2002) J. of Chromatography A. 961:237-244.
Pravdova et al. (2002) Analytica Chimica Acta 456:77-92.
Kassidas et al. (1998) AIChE Journal 44(4):864-875.
Grung & Kvalheim (1995) Analytica Chimica Acta 304:57-66.
Prazen et al. (Jan. 15, 1998) Anal. Chem. 70:218-225.
Sakoe & Chiba (2002) IEEE Transactions on Acoustics, Speech and Signal Processing ASSP26(1):43-49.
Constantino, et al., 2001 "Single-Molecule Detection Using Surface-Enhanced Resonance Raman Scattering and Langmuir-Blodgett Monolayers," Anal. Chem., vol. 73, pp. 3674-3678.
Doering et al., 2002, "Single-Molecule and Single-Nanoparticle SERS: Examining the Roles of Surface Active Sites and Chemical Enhancement," *J. Phys. Chem. B.*, 106:311-317.
Ha, T., 2001, "Single-Molecule Fluorescence Resonance Energy Transfer," *Methods*, 25:78-86.
Kneipp et al., 1997, "Single Molecule Detection Using Surface-Enhanced Raman Scattering (SERS)," *Physical Review Letters*, 78(9):1667-1670.
Kneipp et al., 1999, "Ultrasensitive Chemical Analysis by Raman Spectroscopy," *Chem. Rev.*, 99:2957-2975.
Martens et al., 1999, "A Generic Particle-Based Nonradioactive Homogeneous Multiplex Method for High-Throughput Screening Using Microvolume Fluorimetry," *Analytical Biochemistry*, 273:20-31.
Mulvaney, et al., 2000 "Raman Spectroscopy," Proc. Anal. Chem., vol. 72, pp. 145R-157R.
Mulvaney et al., 2003, "Glass-Coated, Analyte-Tagged Nanoparticles: A New Tagging System Based on Detection with Surface-Enhanced Raman Scattering," *Langmuir*, 19:4784-4790.
Nie et al., 1997, "Probing Single Molecules and Single Nanoparticles by Surface-Enhanced Raman Scattering," *Science*, New Series, 275(5303):1102-1106.
Rossetti et al., 1982, "Electron-Hole Recombination Emission as a Probe of Surface Chemistry in Aqueous CdS Colloids," *J. Phys. Chem.*, 86:4470-4472.
Steigerwald et al., 1988, "Surface Derivatization and Isolation of Semiconductor Cluster Molecules," *J. Am. Chem. Soc.*, 110:3046-3050.
Swartzman et al., 1999, "A Homogeneous and Multiplexed Immunoassay for High-Throughput Screening Using Fluorometric Microvolume Assay Technology," *Analytical Biochemistry*, 271:143-151.
Tibbe et al., 1999, "Optical Tracking and Detection of Immunomagnetically Selected and Aligned Cells," *Nature Biotechnology*, 17:1210-1213.
Wyant et al., 2001, "Whole Blood Microvolume Laser Scanning Cytometry for Monitoring Resting and Activated Platelets," *Platelets*, 12:309-318.
Baumgarth et al., 2000, "A Practical Approach to Multicolor Flow Cytometry for Immunophenotyping," J. Immunol Methods, 243(1-2):77-97.
Beavis et al., 1996, "Allo-7: A New Fluorescent Tandem Dye for Use in Flow Cytometry," Cytometry 24(4):390-395.
Berlier et al., 2003, "Quantitative Comparison of Long-Wavelength Alexa Fluor Dyes to Cy Dyes: Fluorescence of the Dyes and Their Bioconjugates," J. Histochem Cytochem, 51(12):1699-1712.
Beu et al., 2004, "Broadband Phase Correction of FT-ICR Mass Spectra via Simultaneous Excitation and Detection," Anal. Chem., v. 76, pp. 5756-5761.
Bruchez et al., 1998, "Semiconductor Nanocrystals as Fluorescent Biological Labels," Science, 281(5385):2013-2016.
Bucknall et al., 2002, "Practical Quantitative Biomedical Applications of MALDI-TOF Mass Spectrometry", J. Am. Soc. Mass Spectrom. 13:1015.
Bylund, 2001, "Chemometric Tools for Enhanced Performance in Liquid Chromatography—Mass Spectrometry," Acta Univ. Ups., Comprehensive Summaries of Uppsala Dissertations from the Faculty of Science and Technology, 07. 47 pp. Uppsala. ISBN 91-554-4946-8.

Cagney et al., 2002, "De Novo Peptide Sequencing and Quantitative Profiling of Complex Protein Mixtures Using Mass-Coded Abundance Tagging", Nat. Biotech. 20:163.
Caprioli et al., 1972, "Use of Stable Isotopes", Biochem. Appl. Mass Spectrom. 27:735.
Coons, 1961, "The Beginnings of Immunofluorescence," J. Immunol, 87:499-503.
De Rosa et al., 2001, "11-Color, 13-Parameter Flow Cytometry: Identification of Human Naive T-Cells by Phenotype, Function, and T-cell Receptor Diversity," Nat. Med., 7(2):245-248.
De Rosa et al., 2003, "Beyond Six Colors: a New Era in Flow Cytometry," Nature Medicine, vol. 9, No. 1, pp. 112-117.
Dietz et al., 1996, "Volumetric Capillary Cytometry: A New Method for Absolute Cell Enumeration", Cytometry 23:177-186.
Elavathil et al., 1996, "Reproducibility of DNA Ploidy and S-Phase Values from Parraffin-Embedded Tissue", Analytical and Quantitative Cytology and Histology, vol. 18, No. 4, 316-322.
Felinger, 1998, "Data Analysis and Signal Processing in Chromatographpy," Data Handling in Science and Technology, vol. 21,pp. 149-152.
Glazer et al., 1983, "Fluorescent Tandem Phycobiliprotein Conjugates- Emission Wavelength Shifting by Energy Transfer," Biophys J, 43(3):383-386.
Ha et al., 1999, "Single-molecule Fluorescence Spectroscopy of Enzyme Conformational Dynamics and Cleavage Mechanism," Biophysics, vol. 96, pp. 893-898.
Hamberg et al., 1973, "Quantitative Studies on Prostaglandin Synthesis in Man", Anal. Biochem., 55:368.
Hastings et al., 2002, "New Algorithms for Processing and Peak Detection in Liquid Chromatography/Mass Spectrometry Data", Rapid Communications in Mass Spectrometry, 16(5):462-465,467.
Holst, 1998, "CCD Arrays, Camera and Displays", 2d Ed., JCD Publishing and SPIE Optical Engineering Press, pp. i-xxiii.
Jeanmeire et al., 1977, "Surface Raman Spectroelectrochemistry Part 1: Heterocyclic, Aromatic, and Aliphatic Amines Adsorbed on the Anodized Silver Electrode," J. Electroanal. Chem., 84:1-20.
Ji et al., 2000, "Strategy for Qualitative and Quantitative Analysis in Proteomics Based on Signature Peptides", J. Chromat. B 745:197.
Kamentsky, 2001, "Laser Scanning Cytometry," Methods Cell. Biol., 63:51-87.
Kantor et al., 1996, "FACS Analysis of Leukocytes," In: Herzenberg LA, Weir DM, Herzenberg LA, Blackwell C, editors, Weir's Handbook of Experimental Immunology, 5th ed. vol. 2. Cambridge, MA: Blackwell Science; p. 49.1-49.13.
Kantor, 2002, "Comprehensive Phenotyping and Biological Marker Discovery," Disease Markers, 18(2):91-97.
Kantor et al., 2004, "Immune Systems Biology: Immunoprofiling of Cells and Molecules," BioTechniques, 36(3):520-524.
Kantor et al., 2004, "Biomarker Discovery by Comprehensive Phenotyping for Autoimmune Diseases," Clinical Immunology, 111:186-195.
Kast et al., 2003, "Noise Filtering Techniques for Electrospray Quadrupole Time of Fluid Mass Spectra," J. Am. Soc. Mass Spectrom., v. 14, pp. 766-776.
Mahalingam, 1996, "Analysis of Surface Density of Expression of Molecules by Flow Cytometry", Cytometry 24:190.
Moore et al., 1993, "Median Filitering for Removal of Low-Frequency Background Drift," Anal.Chem., 65: 188-191.
Mujumdar et al., 1996, "Cyanine-Labeling Reagents: Sulfoindocyanine Succinimidyl Esters," Bioconjug Chem, 7, 356-362.
Nelson et al., 1995, "Mass Spectrometric Immunoassay", Anal. Chem. 67:1153.
Norton et al., 2000, "Cell Enumeration and Characterization in Microvolume Laser Scanning Cytometry: A Multicolor Image Processing Package," IBOS Society of Photo-Optical Instrumentation Engineers, p. 20-30.
Oda et al., 1999, "Accurate Quantitation of Protein Expression and Site-Specific Phosphorylation", Proc. Natl. Acad. Sci, USA 96:6591.
Oi et al., 1982, "Fluorescent Phycobiliprotein Conjugates for Analyses of Cells and Molecules," J. Cell Biol, 93(3):981-6.

Panchuk-Voloshina et al., 1999, "Alexa Dyes, A Series of New Fluorescent Dyes That Yield Exceptionally Bright, Photostable Conjugates," J. Histochem Cytochem, 47(9):1179-88.

Perez et al., 2002, "Simultaneous Measurement of Multiple Active Kinase States Using Polychromatic Flow Cytometry," Nat Biotechnol, 20(2);155-162.

Perez et al., 2004, "Flow Cytometric Analysis of Kinase Signaling Cascades," Methods Mol Biol, 263:67-94.

Perou et al., 2000, "Molecular Portraits of Human Breast Tumours", Nature, vol. 406, pp. 747-752.

Pinajian et al., 1953, "The Isotope Dilution Procedure of Analysis", J. Am. Phar. Assoc., 301-304.

Proceedings of SPIE V, 1997, "Ultrasensitive Biochemical Diagnostics II", The International Society for Optical Engineering, Feb. 10-12, San Jose, CA.

Roederer et al., 1996, "Cy7PE and Cy7APC: Bright New Probes for Immunofluorescence," Cytometry, 24(3):191-7.

Stewart et al., 1999, "Four Color Compensation", Cytometry, vol. 38, No. 4, 161-175.

Van Duyne, 1979, "Laser Excitation of Raman Scattering from Adsorbed Molecules on Electrode Surfaces," In: Moore CB, editor, Chemical and Biochemical Applications of Lasers, pp. 101-185.

Voyksner et al., 1999, "Investigating the use of an Octupole Ion Guide for Ion Storage and High-pass Mass Filtering to Improve the Quatitative Performance of Electro spray Ion Trap Mass Spectrometry," Rapid Commun. Mass Spectrom., v. 13, pp. 1427-1437.

Waggoner et al., 1993, "PE-CY5- A New Fluorescent Antibody Label for Three-color Flow Cytometry with a Single Laser," Ann N Y Acad Sci, 677:185-93.

Walton et al., 2000, "Microvolume Laser Scanning Cytometry Platform for Biological Marker Discovery," Proc.SPIE-Int.Soc.Opt. Eng., 3926:192-201.

Wang et al., 2003, "Quantification of Proteins and Metabolites by Mass Spectrometry Without Isotopic Labeling or Spiked Standards", Anal. Chem. 75:4818.

Watson et al., 2003, "Lighting up Cells with Quantum Dots," Biotechniques, 34(2):296-300, 302-3.

Wu et al., 2003, "Immunofluorescent Labeling of Cancer Marker Her2 and Other Cellular Targets with Semiconductor Quantum Dots," Nat Biotechnol, 21(1):41-6.

Zuck et al., 1999, "Ligand-receptor Binding Measured by Laser-scanning Imaging," Proc. Natl. Acad. Sci., 96(20):11122-11127.

* cited by examiner

DISPOSABLE OPTICAL CUVETTE CARTRIDGE WITH LOW FLUORESCENCE MATERIAL

RELATED APPLICATIONS

This application is a continuation of U.S. patent application Ser. No. 10/421,638, "Disposable Optical Cuvette Cartridge with Low Fluorescence Material," filed Apr. 22, 2003 now U.S. Pat. No. 6,937,330, which is a continuation-in-part of U.S. patent application Ser. No. 09/552,872, "Disposable Optical Cuvette Cartridge," filed Apr. 20, 2000 now U.S. Pat. No. 6,552,784, which is incorporated herein by reference, and which claims priority from the following U.S. provisional applications, all filed Apr. 23, 1999, and all of which are incorporated herein by reference: U.S. Provisional Application No. 60/130,876, "Disposable Optical Cuvette Cartridge"; U.S. Provisional Application No. 60/130,918, "Spectrophotometric Analysis System Employing a Disposable Optical Cuvette Cartridge"; and U.S. Provisional Application No. 60/130,875, "Vacuum Chuck for Thin Film Optical Cuvette Cartridge." The text of each of the foregoing applications is herein incorporated by reference in its entirety.

FIELD OF THE INVENTION

The present invention relates generally to a disposable optical cuvette cartridge for spectrophotometric measurements of biological samples such as whole blood. More particularly, it relates to a cartridge constructed from a low-fluorescence polymer that contributes minimally to a detected sample fluorescence signal.

BACKGROUND OF THE INVENTION

Optical cuvettes are containers for holding liquid samples during spectrophotometric measurements. As such, they must be at least partially transparent to the relevant wavelengths of light and have well-defined optical path lengths. In some cases, the cuvettes are designed to facilitate high-throughput applications with specific instruments. When used for making measurements on biological samples, they should allow for accurate measurements on small sample volumes. Fluids such as blood require particularly small optical path lengths to prevent measurement contamination resulting from light scattering and absorption by cellular components.

U.S. Pat. No. 5,430,542, issued to Shepherd, discloses a disposable optical cuvette used for holding whole blood during spectrophotometric measurements. The cuvette is formed from two optically transparent liquid-impermeable plastic sheets sandwiching a third "sticky" sheet that has a cutout defining an optical chamber. Inlet and vent ports are also formed in the sticky sheet. A sample to be analyzed is inserted through the inlet port, and the thickness of the middle layer defines the optical path length. One drawback of these cuvettes is that while a large number of them can be manufactured simultaneously, the individual cuvettes are separated for subsequent use, so that only one sample can be analyzed at a time. Separating the cuvettes is necessary because of the placement of the inlet and vent ports in the middle layer. The cuvette is therefore not suitable for rapid and automated measurements on a large number of samples.

An additional problem with these and other cuvettes is that the optical properties of the material used to form the cuvette may interfere with the measurements being performed. For example, when fluorescence measurements are acquired, background fluorescence of the material must be subtracted from the total measurements to obtain the true sample fluorescence.

There is a need, therefore, for a cuvette useful for automated, high-throughput spectrophotometric measurements on small volumes of biological fluid. There is also a need for a cuvette that interferes minimally with the measurements being performed.

SUMMARY OF THE INVENTION

The present invention provides a disposable optical cuvette for spectrophotometric measurements, particularly fluorescence measurements, that allows for accurate, high-throughput measurements on biological fluids requiring small optical path lengths. Additionally, the invention provides methods for manufacturing the cuvette as well as analytical systems and methods employing the cuvette.

In one embodiment, the invention provides a disposable cuvette cartridge for optical measurements of analytes in liquid samples. The cartridge is made from three flat, flexible sheets. The middle one is a flat adhesive or adhesive-coated sheet having a selected thickness defining an optical path length perpendicular to the plane of the flat sheet. A portion of the adhesive sheet is cut out to define at least one optical sample chamber of a desired length. The sample chamber is completed when the adhesive sheet is placed between and sealed to a first flat sheet and a second flat sheet, both of which are preferably impermeable to the sample liquid and transparent to the wavelength of interest. Preferably, at least one of the first and second flat sheets is made of a material having low fluorescence, such as a cyclo-olefin copolymer. The first flat sheet contains an inlet hole and a vent hole that provide access to the optical chamber in the adhesive layer. The vent hole is located adjacent to one end of the chamber and the inlet hole adjacent to an opposite end. Preferably, the cuvette cartridge contains a plurality of optical chambers (e.g., between 2 and 500) and corresponding inlet and vent hole pairs.

The present invention also provides a system for spectrophotometric measurements of liquid samples. In addition to the optical cuvette cartridge, the system contains a light source (e.g., a laser) capable of illuminating a sample contained within the optical chamber of the cuvette cartridge, thereby inducing fluorescence emission from the sample. It also contains a detector for detecting the sample fluorescence that propagates through the low-fluorescence material of the cuvette cartridge.

In an alternative embodiment, the present invention provides a method for manufacturing a disposable cuvette cartridge for use in the spectrophotometric analysis of liquid samples. This method involves sealably bonding or adhering three flat layers to one another in parallel alignment. First and second flat layers, both substantially impermeable to the liquid sample, are provided. The first sheet has a low fluorescence, and one of the two sheets has at least one pair of inlet and vent holes. A flat adhesive sheet is also provided. The flat adhesive sheet has a selected thickness defining an optical path length and at least one cut out portion that defines an optical chamber. The three sheets are aligned so that the inlet hole and vent hole are adjacent to the optical chamber, and the three sheets are caused to adhere together, e.g., by providing pressure to the sheets.

The present invention also provides a method for spectrophotometric measurement of an analyte in a liquid sample. First, a disposable optical cuvette cartridge as described above is provided. A volume of sample is introduced into an optical chamber of the cartridge through an inlet hole. The optical chamber is illuminated with a light source capable of causing fluorescence emission in the sample, and the emission is detected by a detector.

DETAILED DESCRIPTION OF THE INVENTION

The present invention provides a disposable optical cuvette cartridge useful for spectrophotometric measurements of analytes in biological samples such as whole blood. The cuvette holds multiple liquid samples and can be filled rapidly and easily, facilitating high-throughput applications. Preferably, it is manufactured from a material having low fluorescence at the wavelengths of interest, so as not to interfere with the fluorescence measurements being made.

Figure 1:
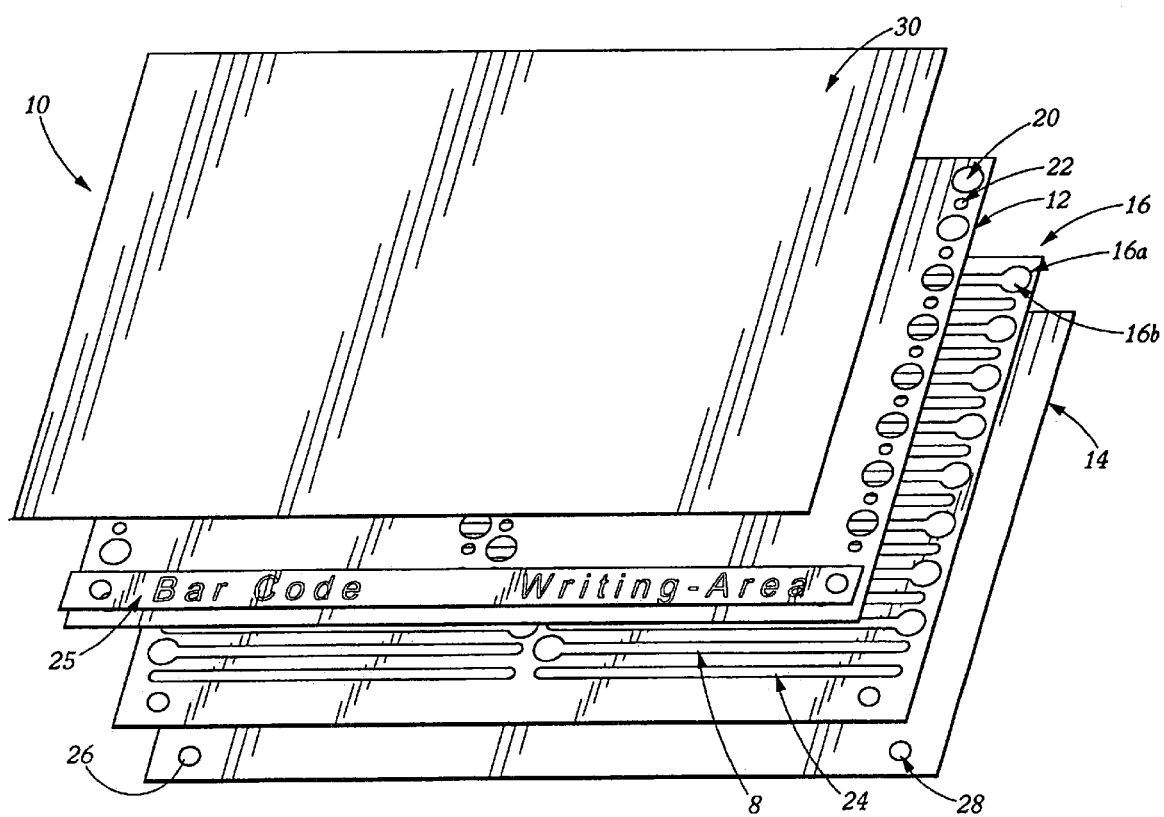
FIG. 1 is an exploded perspective view of a cuvette cartridge of the present invention.
Figure 2:
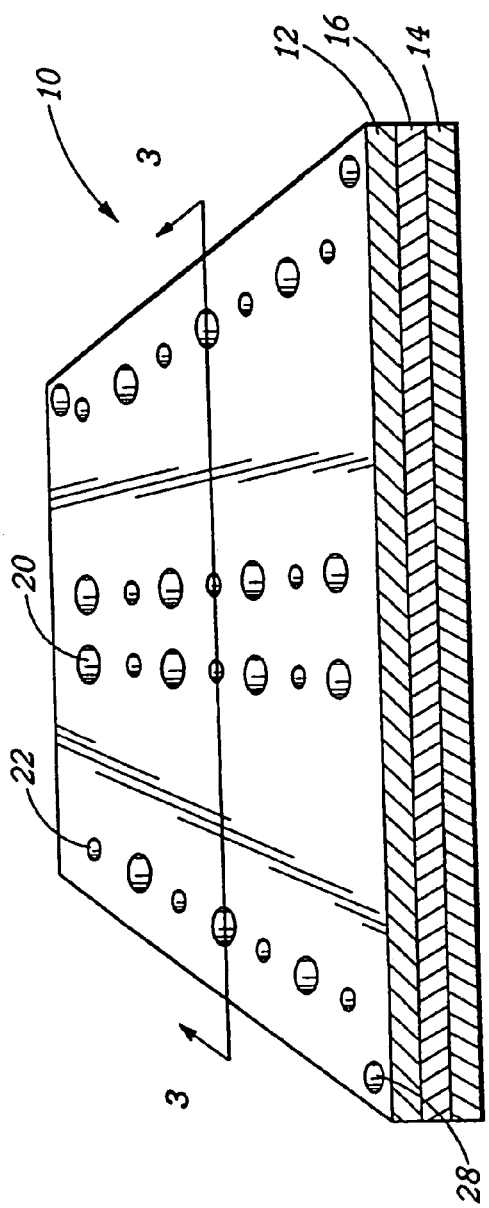
FIG. 2 is a perspective view of an assembled cuvette cartridge of the present invention.
Figure 3:
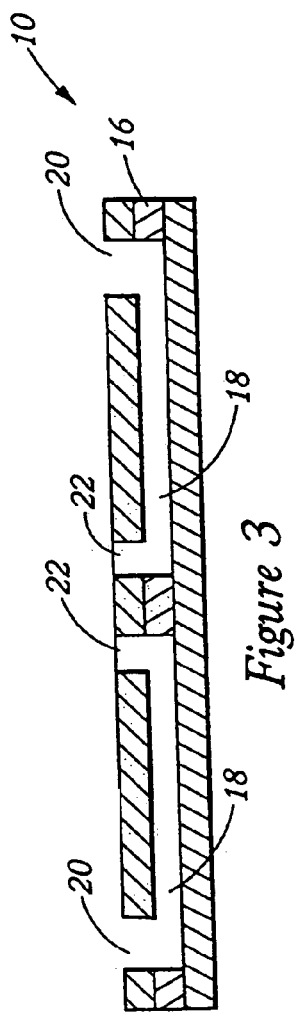
FIG. 3 is a cross-sectional view at 3-3 of the cuvette cartridge of FIG. 2.

FIGS. 1, 2, and 3 show an optical cuvette cartridge 10 of the invention. The cuvette cartridge 10 contains two substantially flat sheets 12 and 14 that are substantially liquid impermeable. That is, the sheets 12 and 14 contain and are not noticeably affected by or permeable to liquid samples that are placed inside the cuvette for analysis. Additionally, the sheets are preferably flexible, non-rigid, plastic films. One, and typically both, of the sheets 12 and 14 are transparent, i.e., substantially optically transmissive, transmitting at least about 25% and preferably at least about 50% of incident light at wavelengths used during spectrophotometric analysis.

Since many of the spectrophotometric analysis techniques that can be carried out using the cuvette cartridge 10 of the invention involve laser stimulation of fluorescence in the samples, the material used to make the plastic film of at least one of the flat sheets 12 and 14 preferably has a low fluorescence in the excitation and emission wavelength ranges of the experiment. That is, the fluorescence intensity of the material is small (e.g., less than 5%) in comparison to the fluorescence-intensity of the sample. It is most important that the sheet through which the sample fluorescence propagates to reach the instrument detector is made of low-fluorescence material. However, both sheets 12 and 14 are preferably made of low-fluorescence material.

Fluorescence can be quantified using a fluorimeter, an instrument that excites a sample with light of varying wavelengths and detects the resulting fluorescence emission at varying wavelengths. Measured fluorescence is typically reported in arbitrary units or as a normalized value, e.g., with respect to the fluorescence of fused silica, known to have a very low intrinsic fluorescence over a large wavelength range. Preferably, the material used to form the sheets 12 and 14 has a fluorescence that is at most four times the fluorescence of a 150-μm thick sheet of fused silica. More preferably, the fluorescence is at most equivalent to the fluorescence of a 150-μm thick sheet of fused silica.

The intensity of the background fluorescence of the low-fluorescence material varies with the excitation and emission wavelengths used, but is preferably low over a wide range of wavelengths. It is most important that the fluorescence be low at the excitation and emission values of the fluorophores used. Common fluorophores used in biological measurements are excited and emit in the red region of the spectrum, i.e., at wavelengths greater than 600 nm. For example, the fluorophores Cy5, Cy5.5, and Cy7 are excited at wavelengths of 649, 675, and 743 nm, respectively, and have emission peaks at 670, 694, and 767 nm, respectively. These three fluorophores can be excited using a helium-neon laser, which has a wavelength of 633 nm. Other common lasers used are argon-krypton lasers, with wavelengths of 488, 568, and 647 nm. Because it is expected that newly developed optical tags will be excited and emit at different frequency ranges, it is desired that the material have low fluorescence over a large range of excitation wavelengths, e.g., from 300 to 700 nm.

The present inventors have investigated the fluorescence properties of potentially suitable materials and determined that cyclo-olefin copolymers (also referred to as cyclic olefin or cycloolefin polymers or copolymers) have the desired optical properties, low fluorescence and high transmittance, at the wavelengths of interest. For example, a suitable material for one or both of the sheets 12 and 14 is the Zeonor® family of cyclo-olefin copolymers, available from Nippon Zeon Co., Ltd., Tokyo, Japan. Additional suitable cyclo-olefin copolymers include Topas®, available from Ticona, Frankfurt, Germany. These materials were originally manufactured for electronic and optical applications, for which fluorescence properties are not relevant. For the present invention, the polymer material is extruded as a sheet or film having the desired thickness.

The two sheets 12 and 14 have a thickness selected to ensure sufficient light transmission through the sheets while providing suitable structural stability of the cuvette cartridge 10. In addition, the sheet thickness should not cause undue manufacturing difficulties. Typical thicknesses range from about 0.25 mils (6.3 μm) to 25 (640 μm) or even 100 mils (about 2.5 mm) or more. Preferably, the thickness is between about 0.5 and 25 mils, and most preferably about 10 mils (about 250 μm). Although the sheets are shown as substantially rectangular in shape, the actual shape can be varied to adapt the resulting cuvette cartridge to fit the desired spectrophotometric analysis apparatus.

The two sheets 12 and 14 are spaced apart from one another and adhesively secured together by an intermediate adhesive layer 16, which has one or more discontinuities or cutouts 16a, areas where the layer 16 has been cut away or is otherwise not present. These areas provide sample zones or optical chambers 18 (FIG. 3) having an optical path length determined by the thickness of the layer 16, which is preferably between about 50 and 200 μm, more preferably between about 75 and 175 μm, and most preferably about 125 μm. The optical chambers are accessed by inlet holes 20 and vent holes 22 in the sheet 12. The inlet hole 20 is positioned adjacent to one end of the optical chamber 18, and the vent hole 22 is positioned adjacent to the other end.

The intermediate adhesive layer 16 can be provided by an accurately laid down layer of a dimensionally-stable adhesive such as a pressure-sensitive acrylic adhesive, pressure-sensitive butylene polymer adhesive, silicone adhesive, or hot melt thermoplastic adhesive. The adhesive layer 16 can be printed upon one of the sheets 12 and 14 in a pattern providing the desired discontinuities, e.g., by conventional techniques such as silk screening, lithography, or printing from an x-y adhesive dispenser. In this case, the layer 16 is printed on one of the sheets 12 and 14, and thereafter the second of the sheets 12 and 14 is laminated on top of the adhesive layer 16. The adhesive can be laid down as a liquid or as a semisolid and can be cured in place partially before the additional layer is added or cured in place after the top and bottom layers are in place, as long as care is taken to maintain the proper spacing between the layers (e.g., by placement of spacer elements) and to ensure that the integrity of the discontinuities defining the sample zones is maintained. Curing can be effected by, e.g., light, heat, or ultraviolet radiation, depending upon the particular adhesive employed.

Alternatively, in a preferred embodiment, the layer 16 is a preformed sheet of adhesive or a preformed sheet of polymer coated on both sides with an adhesive. Any adhesive that bonds to the sheets 12 and 14 without being adversely affected by or adversely affecting the liquid sample can be used. Examples include acrylic adhesives, cyanoacrylates, silicones, epoxies, esters, poly(olefin)-based adhesives, and the like. In a currently preferred embodiment, the adhesive layer 16 is made from a polyester sheet of approximate thickness 3 mils coated on both sides with approximately 1 mil of adhesive. An adhesive-coated sheet is much more structurally stable than a layer made of adhesive only and therefore makes manufacturing of the cuvette cartridge much easier. For example, it is much easier to cut and align the layers when the adhesive layer 16 is more structurally stable.

The cutouts 16a are formed by cutting out portions of the layer 16, e.g., by laser, rotary, or matched metal pattern die cutting, to provide a readily removable piece 16b having the desired contour of an optical chamber 18. The inlet holes 20 and vent holes 22 are cut into the flat sheet 12, for example, by punching.

After the patterns have been formed, the adhesive sheet 16 is applied to one of the flat sheets 12 and 14, and the removable cut piece 16b is peeled off. The other flat sheet is then applied over the adhesive sheet 16. The three sheets 12, 14, and 16 are pressed together. The adhesive sheet 16 holds the two flat sheets 12 and 14 together, providing a liquid-tight seal and forming an optical chamber 18 of defined volume, shape, and optical path length. The flat sheet 12 is placed over the adhesive sheet 16 such that the inlet hole 20 is located adjacent to one end of the optical chamber 18 and the vent hole 22 is located at the other end of the optical chamber.

When the cuvette cartridge 10 is used, each of the sample chambers 18 is filled with a sample for spectrophotometric analysis. A drop of liquid sample, typically between about 5 and about 50 microliters, and preferably approximately 15 microliters, is placed on top of the inlet hole 20. The drop is held together by its surface tension, and capillary action resulting from the cross-sectional area of the sample chamber 18 and the wettability of the chamber surface draws the sample into the chamber 18. Excess sample remains at the inlet hole 20 and can be removed if desired. Note that this mechanism obviates the need for a well-defined sample volume or for accurate measurement of the drop applied to the hole. Liquid samples that can be used in the cuvette cartridge 10 include but are not limited to blood, serum, urine, saliva, homogenate of cells or tissue, suspension of cells or tissue or constituents thereof, analytes in a reaction mixture, solutions of analytes, or any combinations of these.

A cover 30 can be placed over the flat sheet 12 after filling of the inlet ports to reduce evaporation of the samples or other loss. The cover 30 is preferably fabricated from the same materials as the flat sheets 12 or 14. The inlet ports can instead be covered with tape or other material to prevent sample evaporation. Of course, the tape or other material should be applied so as not to obscure measurement of the sample in the optical chamber.

The wettability or surface tension of the sheets 12 and 14 is generally important because it determines whether and how quickly sample liquid (typically aqueous) is drawn into the optical chamber 18. If the sheets are not sufficiently hydrophilic, then it is either impossible to fill the optical chambers with liquid sample, or the chambers fill much more slowly than is desirable. Partially filled chambers are particularly detrimental when measuring a sample such as blood, which contains cells. If the chamber does not fill completely, the cells are not distributed evenly in the sample and their concentration in the blood in the chamber is therefore not representative of their true concentration in the sample.

Many of the materials having desirable optical properties to form the sheets 12 and 14 are not sufficiently hydrophilic to encourage the sample to fill the chamber 18. In fact, the low-fluorescence cyclo-olefin copolymer materials such as Zeonor® have very high water impermeability and are extremely hydrophobic. As is well understood in the art, the wettability of a plastic film can be altered by chemically treating the surface of the film, physically modifying the surface, or plasma treating the surface. Any of these treatments can be employed to provide surfaces with a sufficient degree of hydrophilicity to permit the liquid to be drawn into the sample chambers. Depending upon the materials and samples used, different levels of sample treatment are required. Plasma treatment is the currently preferred technique for rendering the cyclo-olefin copolymer surface more hydrophilic.

Note that the adhesive layer 16 only contributes to the edges of each sample chamber 18, and therefore provides much less contact area for the sample than do the flat layers 12 and 14. It therefore makes a relatively insignificant contribution to the ability of the sample to fill the chamber. However, many adhesives outgas, generating volatile substances that coat the surfaces of the layers 12 and 14 within the same chamber, rendering these surfaces more hydrophobic. One way to address this problem is to store the cuvette cartridge at a low temperature, e.g., in a laboratory freezer, to minimize the volatility of the substances. When the adhesive layer 16 is made from a coated polymer film, however, the adhesive surface area exposed to the chamber is reduced. In this case, as determined by the present inventors, the amount of volatile substances generated does not appreciably reduce the hydrophilicity of the layers 12 and 14, and the cuvette cartridge can be stored at room temperature for extended periods of time (e.g., months).

Another factor determining whether the liquid will be drawn into the chamber 18 is the cross-sectional area of the chamber 18. The width of the cutout region 16b and the thickness of the adhesive sheet 16 define the cross-sectional area of the chamber 16. The thickness is selected taking into account the strong light absorption and scattering of blood as well as the effect of the cross-sectional area on the capillary action.

One advantage of the cuvette cartridge 10 of the present invention is its ability to incorporate a plurality of sample zones or optical chambers in a single unit. Thus, while the cartridge can include a single optical chamber 18, one cuvette cartridge preferably provides between two and about 500 optical chambers 18. Of course, the cuvette cartridge can include many more than 500 chambers if desired. Typically, the number and configuration of sample chambers 18 depend upon the instrument used to perform the measurements. It is anticipated that future high-throughput instruments will allow for a higher density of sample zones, and the cuvette cartridge of the present invention can be modified easily for such applications.

Figure 4:
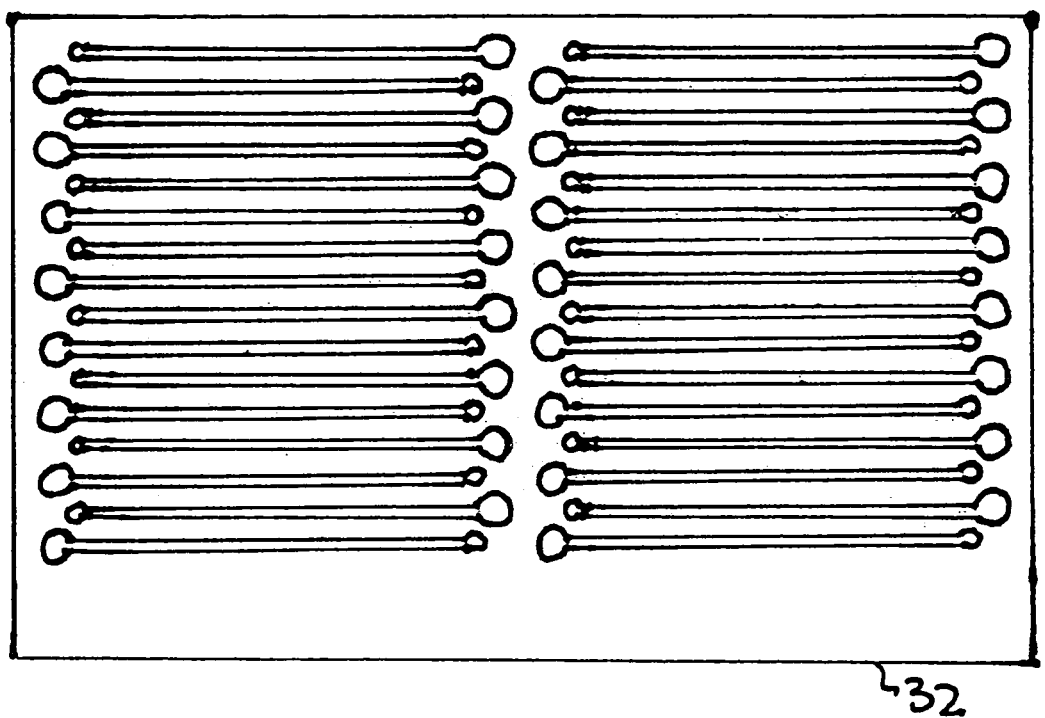
FIG. 4 is a top plan view of an alternative embodiment of an adhesive layer of the cuvette cartridge of FIGS. 1-3.

In many current applications, it is preferable for the cartridge to have between about 8 and about 100 optical chambers, and more preferably from about 30 to about 50 optical chambers. As shown in FIGS. 1-3, this number of chambers is provided by locating the desired number of removable pieces 16b on the adhesive sheet 16 and a corresponding number of inlet and vent holes on the flat sheet 12. The inlet and vent holes can be staggered or arranged in an antiparallel orientation, as indicated in FIG. 1, to provide, for example, closer spacing of optical chambers on the flat sheet. In a particularly useful embodiment, the center-to-center spacing of inlet holes is approximately 9 mm, for ease in filling with a multi-channel pipette. In some cases, it is useful for manufacturing ease to position the inlet and vent holes in a slightly offset fashion, as illustrated by the adhesive layer 32 in FIG. 4. This configuration allows for a higher tolerance in cutting the adhesive layer 32 and the flat sheet 12.

In some embodiments, at least one additional optical chamber 24 (FIG. 1) is provided in the cartridge as a reference or calibration aide. This reference chamber 24 may optionally lack an inlet hole 20 and/or vent hole 22 and can either remain empty to serve as a calibration blank or contain a calibration solution or other standard. Measurement of the blank or standard is used to calibrate measurements from samples in the remaining optical chambers 18. For example, the standard can be a solution of a dye having known optical properties. Alternatively, one of the sample chambers 18 can serve as a reference chamber, and a dedicated reference chamber 24 is not needed. An entire empty cartridge can be used for calibration instead, allowing all of the sample chambers 18 to be used.

As desired, various identification labels 25 can be added to the cartridge 10, preferably in a location that does not interfere with measurement acquisition from the sample chambers 18. For example, in cases in which the two flat sheets 12 and 14 and the adhesive layer 16 have the same dimensions, a label such as a bar code can be applied near an edge 29 of the flat sheet 12. In a currently preferred embodiment, the adhesive sheet 16 is formed from an adhesive-coated polyester film and is larger than the flat sheets 12 and 14, extending past the front edge 29. The extended portion can be covered with a non-adhesive cover if desired. The label is then attached to the adhesive sheet 16 or its non-adhesive cover.

It will be appreciated that the disposable cuvette cartridge of the present invention, with its extremely small sample volumes and flexible construction, requires very precise spectrophotometric measurement methodologies to give accurate information concerning the samples. To this end, it can be important in some cases to accurately and precisely position the cuvette cartridge in the optical measurement apparatus.

In some embodiments, pinholes 26 and 28 are provided to assist in the registration of the cartridge on a platform during an optical measurement. Such pinholes are sized to engage locating pins present in the optical measurement system and typically range from about 1/32 inch to about 1/4 inch, and are preferably about 1/8 inch, in diameter. Preferably, the adhesive layer extends forward beyond the two flat sheets 12 and 14, and the pinholes are positioned in the adhesive layer 16. This allows the pinholes to be cut when the cutout regions 16b are formed in the adhesive layer 16. This process can be very accurate and thus ensures accurate and precise placement of the pinholes. Alternatively, the pinholes can be punched in all three layers at the end of the manufacturing process.

Figure 5:
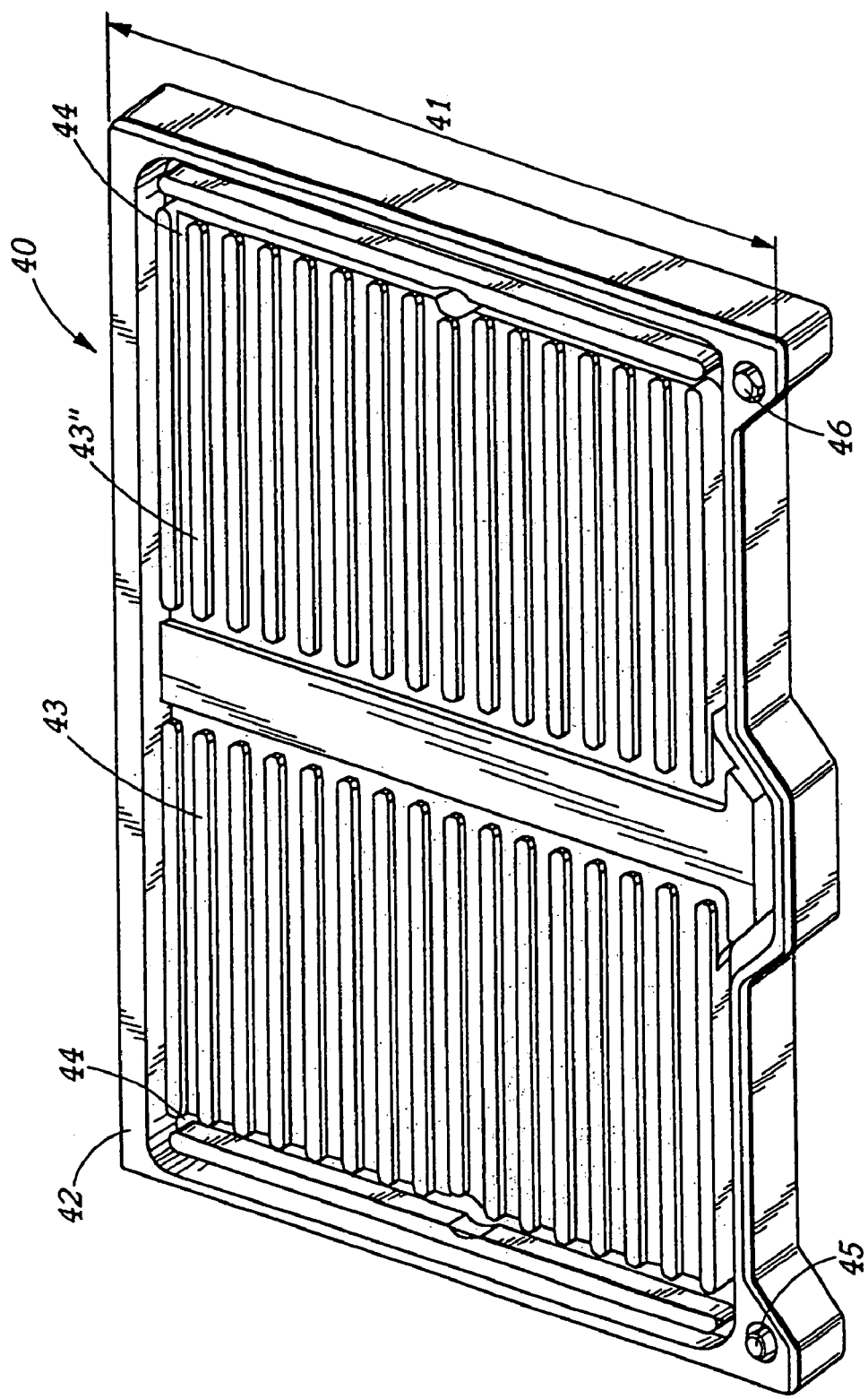
FIG. 5 is a perspective view of a vacuum chuck used to hold the cuvette cartridge of FIGS. 1-3 during spectrophotometric analysis of samples in the cuvette catridge.

FIG. 5 shows a vacuum chuck 40 that serves as a support for the cuvette cartridge 10 during measurement. The vacuum chuck 40 can hold the cassette in accurate registration and in a very well-defined profile such as a very flat profile. The chuck 40 presents a generally flat top surface 41 that includes a continuous perimeter 42 and a series of raised areas 43 making up the flat surface 41 upon which the cuvette cartridge 10 is placed. The top surface 41 also includes a series of depressed areas 44 that are below the plane defined by the perimeter 42 and raised areas 43. When the cuvette cartridge 10 is placed onto the chuck 40, the pinholes 26 and 28 in the cartridge are aligned with pins 45 and 46 to accurately register the cartridge 10. A vacuum is applied to the volume defined by the depressed areas 44. This pulls the cartridge 10 down onto the chuck 40 and seals it firmly onto the plane defined by the raised areas 43 and perimeter 42.

The vacuum chuck 40 is fabricated out of a material such as metal, plastic, glass, or ceramic that is stable and nonreactive with the cuvette cartridge 10, and preferably also with the sample liquid. In one embodiment, the vacuum chuck 40 is mounted on an optical measurement device such as a laser fluorescence scanner. Use of such a vacuum chuck 40 is advantageous in that the cuvette cartridge 10 is held flat against the chuck 40, thereby facilitating focusing of the optical instrument and reducing the need to refocus during measurements in multiple optical chambers of the cuvette cartridge 10. Furthermore, the use of a vacuum chuck 40 to hold the cartridge 10 flat obviates any requirement that the cartridge itself be rigid and thus allows the use of flexible materials for the cartridge 10. It will be appreciated by those of skill in the art that the vacuum chuck 40 should be constructed and employed in ways that cause the cuvette cartridge to reproducibly present a consistent optical path through the various sample and calibration chambers. To this end, it is generally desirable to check the degree of vacuum drawn in the vacuum chuck and the spacing of the vacuum zones in the chuck to ensure that when a particular cuvette cartridge is placed on the vacuum chuck and held in place, there is not an unacceptable degree of distortion.

When the vacuum chuck 40 and cuvette cartridge 10 are used in an optical instrument such as a spectrophotometer, the samples in the cuvette cartridge can be scanned with a laser, and the contents of the sample determined or quantified by reference to the fluorescence emanating from the sample. In this case, it is advantageous to minimize background fluorescence, including fluorescence generated by the materials from which the chuck 40 is fabricated. To do so, the chuck 40 can be fabricated with depressed areas 44 in the form of slots aligned with and positioned directly beneath the optical chambers on the cartridge 10 when the cartridge 10 is placed on the vacuum chuck 40. Such slots can reduce fluorescence by distancing the material of the chuck from the focal plane of the optical instrument used.

In a typical use of the cuvette cartridge 10 of the invention, a liquid sample is applied to an inlet hole 20, thereby filling the optical chamber 18 by capillary action. The cartridge is placed in a position for an optical measurement, such as on the platform of a laser scanner. A confocal laser scanner is used to scan the optical chamber. Typically, the scanner uses the natural fluorescence of the adhesive sheet to define the edges of the optical chamber. In some cases, a reference optical chamber can be used by the scanner to detect the edges of the optical chamber. These measurements can then be applied to the optical chambers on the cartridge. The material of the adhesive layer 16 often has spectrophotometric properties that are distinguishable from those of the layers 12 and 14. By noting the difference in properties, one can determine accurately when the spectrophotometer is reading the spectrophotometric profile of the sample and when it is reading information for areas outside the sample zone. Similarly, sophisticated automated spectrophotometric readers can locate the edges of the sample zone by noting the properties of the layer 16 and make their readings on the contents of the sample zone safely away from the edges. In addition, it is necessary to focus the detector on the sample itself and not on the flat sheets 12 and 14 above and below the sample. This can be done by recording the fluorescence detected at different vertical levels and locating the fluorescence maximum. Alternatively, a reference point with known optical properties and known vertical distance from the sample (e.g., the surface 41 of the chuck 40) can be selected and used to help focus the instrument.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the disclosed invention.

What is claimed is:

1. An optical cuvette cartridge for use in optical measurements of liquid samples, the cuvette cartridge comprising:

a pair of parallel sheets of material substantially impermeable to the liquid samples, said parallel sheets spaced apart to define a plurality of separated optical chambers wherein a first and a third optical chamber of said plurality of separated optical chambers each comprise an inlet hole that is offset in a longitudinal orientation from a vent hole of a second optical chamber located adjacent to and in between said first and third optical chambers.

2. The optical cuveffe cartridge of claim 1, wherein said pair of parallel sheets are each flexible thin films.

3. The optical cuvette cartridge of claim 1, wherein said optical chambers are formed by an intermediate layer attached to at least one sheet of said pair of parallel sheets.

4. The optical cuvette cartridge of claim 3, wherein the intermediate layer is a layer selected from the group consisting of an adhesive, a flexible thin film, and a flexible thin film bounded on both sides by layers of adhesive.

5. The optical cuvette cartridge of claim 3, wherein the intermediate layer comprises a thickness to cause liquid to flow into said optical chambers by capillary action.

6. The optical cuvefte cartridge of claim 1, comprising between 2 and 500 optical chambers.

7. The optical cuveffe cartridge of claim 1, wherein at least one of the pair of parallel sheets is transparent to a wavelength of interest.

8. The optical cuvette cartridge of claim 7, wherein the wavelength of interest is greater than about 600 nm.

9. The optical cuvette cartridge of claim 1, wherein at least one sheet of the pair of parallel sheets is made of a cyclo-olefin copolymer.

* * * * *